(12) United States Patent
Gorini et al.

(10) Patent No.: US 8,663,159 B2
(45) Date of Patent: Mar. 4, 2014

(54) ENDOSCOPIC DEVICE

(75) Inventors: Samuele Gorini, Montecalvoli (IT); Giuseppe Pernorio, Pisa (IT); Alberto Arena, Cascina (IT)

(73) Assignee: Era Endoscopy S.R.L., Peccioli (Pisa) (IT)

( * ) Notice: Subject to any disclaimer, the term of this patent is extended or adjusted under 35 U.S.C. 154(b) by 230 days.

(21) Appl. No.: 13/139,070

(22) PCT Filed: Dec. 10, 2008

(86) PCT No.: PCT/IT2008/000753
§ 371 (c)(1),
(2), (4) Date: Jun. 10, 2011

(87) PCT Pub. No.: WO2010/067386
PCT Pub. Date: Jun. 17, 2010

(65) Prior Publication Data
US 2011/0245613 A1    Oct. 6, 2011

(51) Int. Cl.
*A61B 1/00* (2006.01)
*A61M 31/00* (2006.01)

(52) U.S. Cl.
USPC ........ 604/95.01; 600/114; 600/139; 600/140; 604/95.03

(58) Field of Classification Search
USPC ......... 600/101, 104, 106, 114–116, 139, 140; 604/95.01–95.05; 606/1
See application file for complete search history.

(56) References Cited

U.S. PATENT DOCUMENTS

| | | |
|---|---|---|
| 5,398,670 A | 3/1995 | Ortiz et al. |
| 5,906,591 A | 5/1999 | Dario et al. |
| 6,017,323 A | 1/2000 | Chee |
| 2002/0103473 A1 | 8/2002 | Roychowdhury et al. |
| 2003/0208183 A1 | 11/2003 | Whalen et al. |
| 2005/0272976 A1 | 12/2005 | Tanaka et al. |
| 2007/0179339 A1* | 8/2007 | Gorini et al. .......... 600/139 |

FOREIGN PATENT DOCUMENTS

EP    1792561    6/2007

OTHER PUBLICATIONS

PCT International Search Report for PCT/IT2008/000753 filed Dec. 10, 2008, in the name of ERA Endoscopy S.R.L.
PCT Written Opinion for PCT/IT2008/000753 filed Dec. 10, 2008, in the name of ERA Endoscopy S.R.L.
Menciassi A et al., "Robotic Solutions and Mechanisms for a Semi-Autonomous Endoscope", Proceedings of the 2002 IEEE/RSJ International Conference on Intelligent Robots and Systems, 1379-1384 (2002).

* cited by examiner

*Primary Examiner* — Matthew J Kasztejna
*Assistant Examiner* — Ryan Henderson
(74) *Attorney, Agent, or Firm* — Steinfl & Bruno, LLP

(57) ABSTRACT

An endoscopic device capable of autonomous locomotion through a body cavity in a pre-established direction of displacement is described. The endoscopic device comprises a tubular body that extends between a front end portion and a rear end portion and a reinforcement structure distributed along the length of the tubular body. Each end portion includes an anchoring means for temporarily and alternately attaching the end portions to a wall of the body cavity.

14 Claims, 3 Drawing Sheets

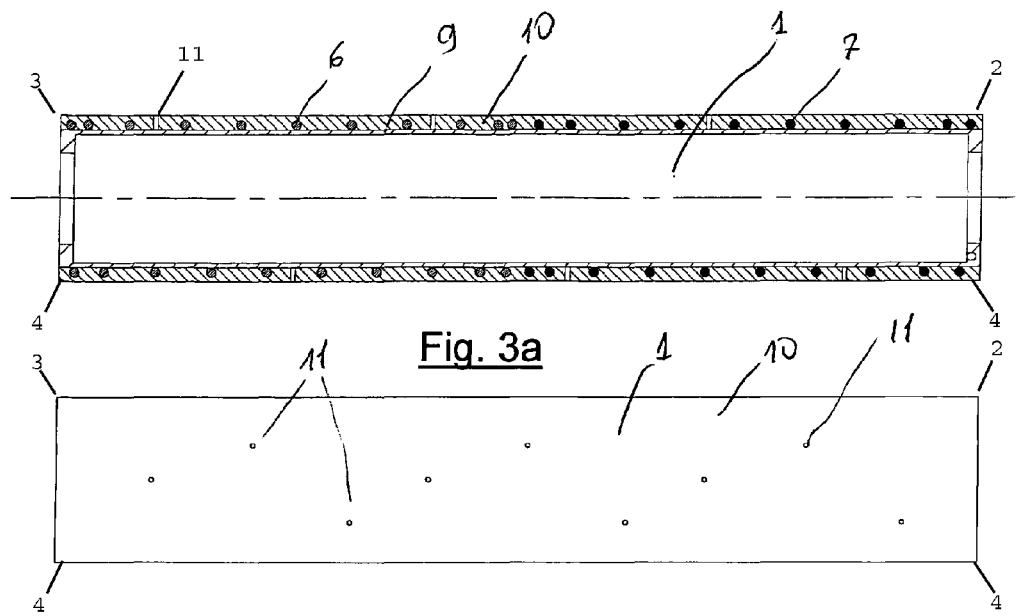
Fig. 3a
Fig. 3b
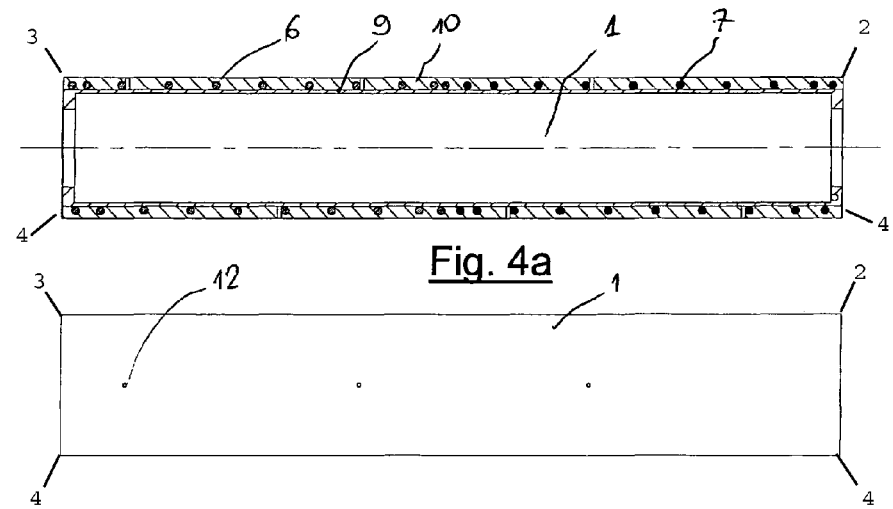
Fig. 4a
Fig. 4b

ENDOSCOPIC DEVICE

CROSS REFERENCE TO RELATED APPLICATIONS

The present application is the US national stage of International Application PCT/IT2008/000753 filed on Dec. 10, 2008.

FIELD OF THE INVENTION

The present invention relates to an improvement to an endoscopic device for locomotion through a tubular body cavity and particularly, but not exclusively, through the gastrointestinal tract, capable of migrating in a pre-established direction by so-called inchworm motion.

BACKGROUND ART

Endoscopic devices for surgical or diagnostic procedures are already known, which are operated by the surgeon who directly imparts to the device its forward motion through the patient's body. These devices are generally associated with surgical and/or diagnostic instruments needed to complete various procedures, e.g. micro-arms, micro-cameras and/or laser emitters.

Endoscopic devices of this type, but capable of autonomous or semi-autonomous locomotion through the body cavity of a patient are described, for instance, in U.S. Pat. No. 5,398,670, U.S. Pat. No. 5,906,591 and WO02/068035. The endoscopic device described in these documents substantially consists of a tubular body of variable length with front and rear end portions equipped with anchoring means that enable said front end portion or rear end portions to become temporarily and alternately attached to the wall of the body cavity, thereby enabling the forward motion of the device.

In particular, the variable-length tubular body of the endoscopic device described in the above-mentioned documents is in the form of a bellows-shaped tube and is consequently capable of being extended or contracted by means of air injected therein or aspirated therefrom. In the above-mentioned patent application PCT n. WO02/068035, the device is anchored to the wall of the body cavity by clamping means associated with the front and rear end portions of the device and selectively enabled by an external control unit in synchronism with the successive extensions and contractions of the bellows-shaped tubular body. The aforementioned clamping means are enabled by pneumatic actuating means that, in the preferred embodiment of the invention, also consist of bellows-shaped members.

When it is extended, a positive pressure is created inside the bellows by means of compressed air, thereby obtaining an elongation proportional to the pressure therein, while the bellows are contracted by progressively reducing the pressure inside the bellows, until some degree of vacuum is created.

In order to overcome the functional limitations of the bellow-shaped endoscopic devices due to its relative extendibility and friction between its outer surface and the walls of the body cavity, which have a negative effect on the device's efficiency of locomotion, EP-A-1792561, in the name of the same applicant, discloses an endoscopic device wherein the tubular body has an high extensibility an a low friction coefficient in such a way to prevent the tissue forming the body cavity wall to be dragged and hence ensuring an effective forward movement of the device.

According to this patent application, the tubular body of the endoscopic device is made of a low hardness elastomeric material, for example Shore A-10 silicone, and incorporates a reinforcement structure distributed along its length that is substantially rigid in the radial direction and yielding in the axial direction. In a particularly preferred embodiment, the reinforcement structure consists of a pair of coaxially aligned springs with coils wound crosswise to one another, incorporated within its thickness. The presence of the springs prevents the tubular body from swelling sidewards, while the inverted winding of the springs prevent the body from rotating during the extension. In another embodiment of the invention the reinforcement structure consists of equally spaced rings coaxially incorporated in the tubular body wall.

The production of the above mentioned tubular body comprises moulding a silicone tubular element, constituting the air containment part, and placing the springs o the array of rings around it. A tubular silicone layer is then moulded on the tubular element to prevent the sliding of the elements forming the reinforcement structure and the direct contact thereof with the intestine tissue.

A production defect, such as a blister or a tearing made during the tubular body extraction from the mould, could cause air to enter between the tubular member and the outer tubular layer thus forming an air bubble.

Due to its chemical nature, silicone does not adhere to metal reinforcement structure within the tubular body wall and, therefore, the interface between the surface of said structure and the silicone material over it forms a preferential channel for flowing out air from the tearing. When the reinforcement structure is formed by helicoidal springs, once air is entered in the meatus between spring coil and silicone, air tends to travel along the spiral all over its length forming a spiral-shaped swelling. When the pressure is high enough, the force acting on the interface is so great as to cause the outer silicone layer to detach from the inner silicone layer, this resulting in the formation of an air bubble as shown in FIG. 1. Depending on its size, the bubble could give raise to a barotrauma, i.e. an injury caused by an excess pressure on the intestine walls caused by air or also an air filled ball. Walls stretch until tearing occurs with consequent pain and bleeding and, in most serious cases, intestine wall breaking. Furthermore, the formation of an air bubble may prevent the device from being withdrawn from the intestine, because it is not sure that if the air flow is stopped, the phenomenon would be reversible. As a matter of fact, the partial reduction of the internal pressure shortens the tubular body and this might cause the closure of the tearing, whereby the air bubble would be kept in an inflated condition.

OBJECTS AND SUMMARY OF THE INVENTION

The object of the present invention is to provide an endoscopic device of the type described in the European patent application no. EP-A-1792561, wherein the extensible body of the device would not be affected by the risk of air bubble formation within the tubular wall which might be dangerous to the person undergone an endoscopic analysis or might hinder the device withdrawal.

A particular object of the present invention is to provide an endoscopic device of the above-mentioned type wherein it would be possible to prevent relative movements between the elements forming the reinforcement structure (coils or rings) during moulding so as to improve the pitch evenness.

These objects are achieved by the endoscopic device according to the present invention, the essential features of which are set forth in claim 1. Further important features are set forth in the depending claims.

According to an important aspect of the invention, the endoscopic device comprises a tubular body made of elastic material incorporating a reinforcement structure distributed over its length and substantially rigid in its radial direction and yielding in the axial direction; the tubular body wall is formed by superimposed inner and outer layers and the reinforcement structure is arranged therebetween. Through openings are formed on the outer layer for enabling air possibly entered between the inner layer and the outer layer form the inside of the tubular body to be discharged to the outside. In this way it is avoided that an air bubble due to production defects may be formed capable of preventing the device sliding and withdrawal.

BRIEF DESCRIPTION OF THE DRAWINGS

The characteristics and advantages of the endoscopic device according to the present invention will be apparent from the following description of some embodiments thereof, given as a non-limiting example with reference to the attached drawings, wherein:

FIGS. 3a and 3b show a longitudinal section and a side view of the extensible body of an endoscopic device according to a first embodiment of the invention;

FIGS. 4a and 4b show a longitudinal section and a side view the extensible body of an endoscopic device according to a second embodiment of the invention;

DETAILED DESCRIPTION OF THE INVENTION

Figure 1:
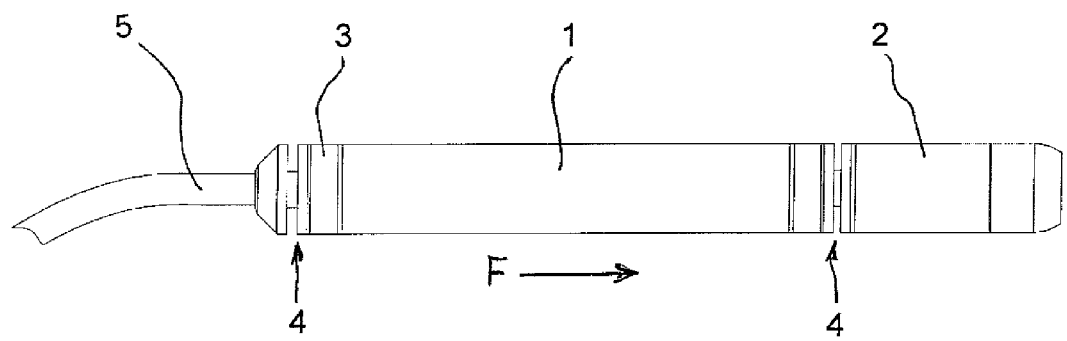
FIG. 1 is a side view of an endoscopic device according to the prior art.

With reference to FIG. 1, a conventional endoscopic device, which the present invention is applicable to, comprises of a tubular body 1 extending between two end portions, called the front 2 and rear 3 end portions respectively, where the terms front and rear refer to the device's direction of locomotion through the body cavity, indicated by the arrow F. Clearly, the device can move both forwards and backwards within the body cavity.

The front 2 and rear 3 end portions of the device include anchoring means 4, specifically of the clamping type, pneumatically actuated in a known way, by means of which the device temporarily and alternately becomes attached to the wall of the body cavity to enable its locomotion in a known manner.

The rear end portion 3 is connected to an external control unit by means of a hose 5, which houses the service tubes, including the tubing needed to deliver compressed air inside the tubular body 1, or to create a negative pressure therein, thereby inducing the extension or retraction of the tubular body 1 that is necessary for the known so-called inchworm type of locomotion.

In order to allow the extension and retraction of the tubular body 1, it is made of a low-hardness elastomeric material, e.g. Shore A-10 silicone. The tubular body 1 has a structural reinforcement comprising a pair of springs 6 and 7 of rigid material, steel for example, having opposed coil winding. Springs 6 and 7 are incorporated inn the wall of tubular body 1 and are axially aligned to one another on the longitudinal axis of body 1.

Figure 2:
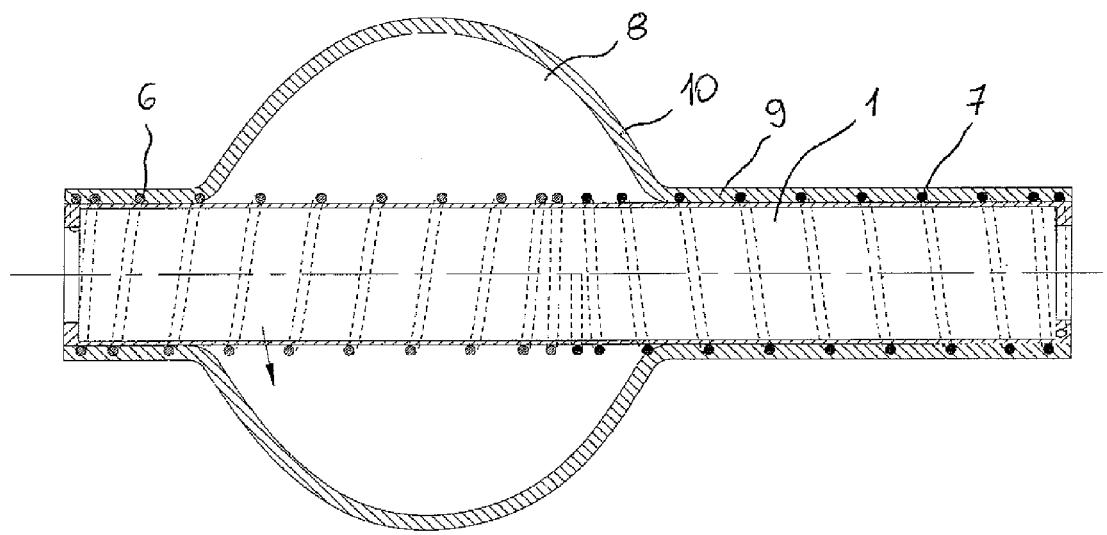
FIG. 2 shows the formation of an air bubble in the extensible body of the endoscopic device of FIG. 1 shown in longitudinal sectional view.
Figure 5A:
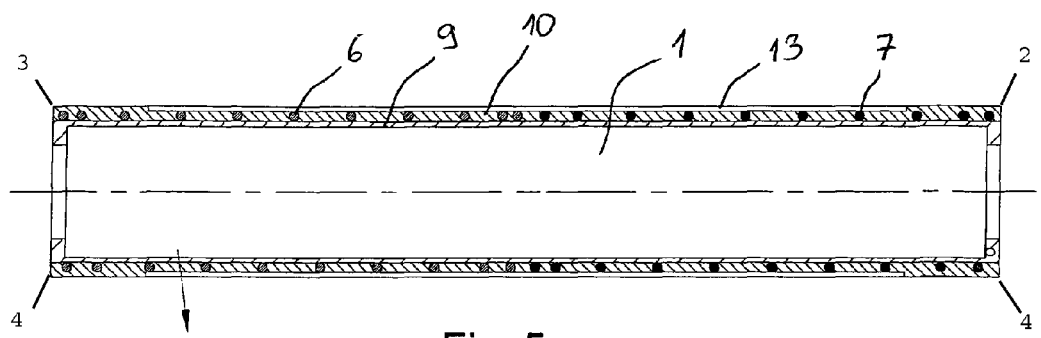
FIGS. 5a and 5b show a longitudinal section and a side view the extensible body of an endoscopic device according to a third embodiment of the invention.

Springs 6 and 7, as well as front 2 and rear 3 portions are shown in FIGS. 3a, 4a and 5a, in which the wall of the extensible tubular body 1 is also shown as being formed by two superimposed layers, indicated as 9 and 10, made of silicone material, while in FIG. 2 there is shown the formation of a dangerous air bubble 8 between the inner layer 9 and the outer layer 10 of the extensible tubular body 1 in an endoscopic device according to the prior art. FIGS. 3a, 4a, and 5a, also show positions for the anchoring means, 4, at the front 2 and rear 3 portions.

According to a first embodiment of the invention, FIGS. 3a and 3b show a plurality of casually distributed holes 11 extending through the outer layer 10 of the tubular body 1 that are formed on the extensible tubular body wall. In this way the size of the air bubbles that could be formed depends on the value of the minimum distance between the holes. In fact, as soon as the bubble size increases beyond this value, the air bubble meets an hole and the extensible tubular body 1 is deflated.

In a second embodiment of the invention shown in FIGS. 4a and 4b, a plurality of holes 12 distributed in such a way to be located in points corresponding to the coils of the springs 6 and 7 situated below are formed on the surface of the tubular body 1. In this case too holes 12 extend through the outer layer 10 of the extensible tubular body wall. The main advantage of this solution as compared to the previous one consists in that the presence of the holes along the surface portion extending over the spring coils allows the air losses to be more quickly blocked. As a matter of fact, as already explained, when an air bubble is formed as a result of a production defect, it certainly reach a coil of the spring and then air runs along the spiral until it comes out of one of the holes.

Moreover, this solution has an additional advantage from the production point of view consisting in that the pins used to form the holes during material moulding allow a more uniform spring pitch to be maintained.

In an embodiment particularly advantageous from the production point of view the extensible tubular body 1 is made in two halves, one of which contains the right-hand spring 6, the other one the left-hand spring 7. The two halves are then end joined through a plastic disk-shaped plate glued to them. Three holes 12 are formed on a side and three holes 12 are formed on the opposite side of each half of the extensible tubular body 1 to prevent air bubble growing. The hole forming pins serve also to keep the spring in position and hence have a constant pitch.

Figure 5B:
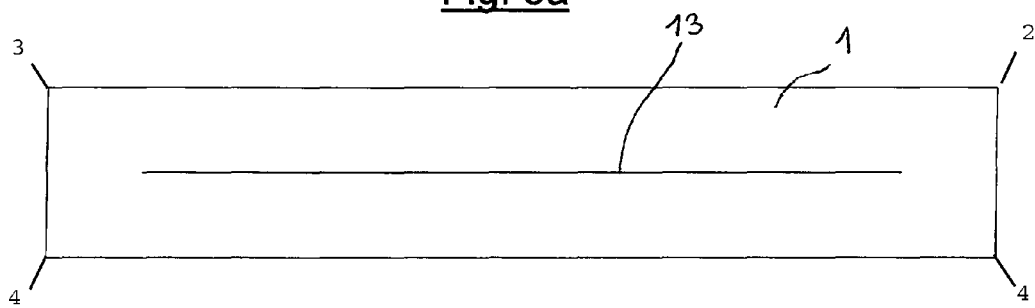

In a third embodiment of the invention shown in FIGS. 5a and 5b, one or more slits extending in a generally longitudinal direction and passing through outer layer 10 are formed on the surface of the tubular body 1. If a production defect is present, the slits allows air to escape directly in the intestine. The patient perceives trouble as a result of air escape and inform the operator who stops the procedure. In this case it is sufficient to remove the device which is anyway deflated and hence there is no risk that, when dragged to the outside, it would be engaged with the intestine loops.

As is known from EP-A-1792561, the reinforcement structure of the tubular body may be formed not only from opposed winding spring, but also, as an alternative, from rings incorporated coaxially in the tubular body wall. Furthermore, in the endoscopic device according to the invention even the actuating device for the anchoring means, as well the one for steering the device head, comprise an elastic tubular body, although with a significantly lower length, incorporating a reinforcement structure of the spring type or the ring type as described above. It is intended that the invention obviously extends even to these components of the endoscopic device.

The endoscopic device according to the present invention may undergo variations and/or modifications without departing from the scope of the invention, as set forth in the following claims.

The invention claimed is:

1. An endoscopic device for self-propelled locomotion through a body cavity in a pre-established direction of displacement, comprising:
  a tubular body made of an elastic material extending between a front end portion and a rear end portion, each end portion comprising respective anchoring means pneumatically actuated and suitable for temporarily and alternately attaching said end portions to a wall of the body cavity in synchronism with corresponding axial extensions and contractions of said tubular body,
  wherein:
  said tubular body comprises a reinforcement structure distributed along its length,
  the reinforcement structure is substantially rigid in a radial direction and yielding in an axial direction, and
  a wall of said tubular body is formed by superimposing an inner layer and an outer layer, said reinforcement structure being arranged there between, wherein one or more through openings are formed on said outer layer, the one or more through openings being adapted to allow air possibly entering between said inner layer and said outer layer from the inside of said tubular body to be discharged to an outside of said tubular body.

2. The endoscopic device as set forth in claim 1, wherein said through openings are through holes randomly distributed on said outer layer.

3. The endoscopic device as set forth in claim 2, wherein said reinforcement structure is formed by two springs axially aligned along the longitudinal axis of the tubular body between said inner layer and outer layer.

4. The endoscopic device as set forth in claim 2, wherein said reinforcement structure is formed by a row of parallel rings axially incorporated between said inner layer and outer layer of said tubular body.

5. The endoscopic device as set forth in claim 1, wherein said through openings are through holes formed on said outer layer at locations corresponding to said reinforcement structure.

6. The endoscopic device as set forth in claim 5, wherein said reinforcement structure is formed by two springs axially aligned along the longitudinal axis of the tubular body between said inner layer and outer layer.

7. The endoscopic device as set forth in claim 5, wherein said reinforcement structure is formed by a row of parallel rings axially incorporated between said inner layer and outer layer of said tubular body.

8. The endoscopic device as set forth in claim 1, wherein said through openings are through slits formed in a generally longitudinal direction on said outer layer.

9. The endoscopic device as set forth in claim 8, wherein said reinforcement structure is formed by two springs axially aligned along the longitudinal axis of the tubular body between said inner layer and outer layer.

10. The endoscopic device as set forth in claim 8, wherein said reinforcement structure is formed by a row of parallel rings axially incorporated between said inner layer and outer layer of said tubular body.

11. The endoscopic device as set forth in claim 1, wherein said reinforcement structure is formed by two springs axially aligned along a longitudinal axis of the tubular body between said inner layer and outer layer.

12. The endoscopic device as set forth in claim 11, wherein the two springs are wound crosswise to one another.

13. The endoscopic device as set forth in claim 11, wherein said reinforcement structure is formed by a row of parallel rings axially incorporated between said inner layer and outer layer of said tubular body.

14. The endoscopic device as set forth in claim 1, wherein said reinforcement structure is formed by a row of parallel rings axially incorporated between said inner layer and outer layer of said tubular body.

* * * * *